(12) United States Patent
Nordin et al.

(10) Patent No.: US 7,964,144 B1
(45) Date of Patent: Jun. 21, 2011

(54) MEMS BIOSENSOR WITH INTEGRATED IMPEDANCE AND MASS-SENSING CAPABILITIES

(75) Inventors: Anis Nurashikin Nordin, Kuala Lumpur (MY); Muhammad Ibn Ibrahimy, Kuala Lumpur (MY); Maizirwan Mel, Kuala Lumpur (MY); Ioana Rodica Voiculescu, New York, NY (US)

(73) Assignees: International Islamic University Malaysia, Kuala Lumpur (MY); City College of New York, New York, NY (US)

( * ) Notice: Subject to any disclaimer, the term of this patent is extended or adjusted under 35 U.S.C. 154(b) by 0 days.

(21) Appl. No.: 12/755,668

(22) Filed: Apr. 7, 2010

(30) Foreign Application Priority Data

Jan. 14, 2010 (MY) .............................. PI2010000171

(51) Int. Cl.
*G01N 15/06* (2006.01)
*G01N 33/00* (2006.01)
*G01N 33/48* (2006.01)
*G01N 27/00* (2006.01)

(52) U.S. Cl. ........ 422/68.1; 422/50; 422/69; 422/82.01; 422/82.02; 436/43; 436/63; 436/64

(58) Field of Classification Search .................... 422/50, 422/68.1, 69, 82.01, 82.02; 436/43, 63, 64
See application file for complete search history.

(56) References Cited

U.S. PATENT DOCUMENTS

| | | | | |
|---|---|---|---|---|
| 5,135,852 A | * | 8/1992 | Ebersole et al. | ................ 435/39 |
| 5,981,268 A | * | 11/1999 | Kovacs et al. | .............. 435/287.1 |
| 7,394,180 B2 | * | 7/2008 | Okaguchi et al. | ............. 310/317 |
| 2005/0043894 A1 | * | 2/2005 | Fernandez | ...................... 702/19 |

* cited by examiner

*Primary Examiner* — Brian J Sines
(74) *Attorney, Agent, or Firm* — Smith, Gambrell & Russell, LLP

(57) ABSTRACT

A biosensor device (1) providing an analysis platform for detecting cell growth, comprising of an aluminium nitride (AlN) base (2), a shear horizontal-surface acoustic wave (SH-SAW) resonator including an input transducer (4) and an output transducer (5) symmetrically positioned on the aluminum nitride (AlN) base (2), a counter electrode (6) positioned parallel to working electrodes (7) on the aluminum nitride (AlN) base (2), for transmitting frequency voltage towards the living cell (3), a plurality of working electrodes (7) positioned beneath the living cell (3) on the aluminium nitride (AlN) base (2) for receiving frequency voltage from the living cell (3), an impedance analyzer (8) for receiving impedance readings from the counter electrode (6) and working electrodes (7), and a back-etched silicon substrate (9) coupled to the aluminium nitride (AlN) base (2), for reducing current loss, wherein the living cell (3) is positioned in between of the input transducer and output transducer on the aluminium nitride (AlN) base (4).

6 Claims, 3 Drawing Sheets

_US 7,964,144 B1_

MEMS BIOSENSOR WITH INTEGRATED IMPEDANCE AND MASS-SENSING CAPABILITIES

TECHNICAL FIELD

The present invention relates to a MEMS biosensor device for providing an analysis platform in detecting cell growth and more particularly by using shear horizontal-surface acoustic wave (SH-SAW) resonator and electric cell-substrate impedance sensing (ECIS) technique.

BACKGROUND ART

Cancer is the second leading cause of death worldwide. It is generally agreed that early diagnosis of the disease is almost always a prerequisite of successful treatment. For decades, cancer diagnostic methods have been based on morphological examination of surgically removed tissues. However, this approach has significant limitations for predicting the progression of the cancer cells such as inaccuracy and requirement for large amounts of biological materials. Furthermore, morphological examination of these cancer cells requires highly trained personnel to be able to distinguish cancer cells from normal cells. Due to these limitations, a number of scientists have developed other types of cancer diagnostic methods, for example a biomarker that uses biological, chemical or biophysical indicator of an underlying biological process to indicate or determine a particular disease state. Another method is by detecting the cell growth using a MEMS (microelectromechanical system) biosensor device that merges biological knowledge and microelectronics technology.

Recently, MEMS technology expands in an extremely fast pace. It is used in various applications such as actuators, accelerometer, pressure sensors, chemosensors, gyroscopes, optical switching technology and more. Nevertheless, MEMS technology is also used in biological fields for the construction of biosensors. Generally, a MEMS biosensor is an analytical device with the combination of biotechnology and microelectromechanical system that converts a biological response to electrical signal. A MEMS biosensor can be used as a device to measure chemicals and micro-organisms in wide range of environments and as a biological system to detect complex materials. Nowadays, MEMS biosensors have become widespread use in a wide variety of applications such as diagnostics, therapeutics and tissue engineering. There are a few types of biosensor used in the industry such as calorimetric, potentiometric, amperometric, surface acoustic wave and more. In calorimetric biosensors, the change in temperature of a solution containing analyte is measured whereby in potentiometric biosensors, electrical potential is produced due to the changed distribution of electrons. As for amperometric biosensors, the analyte undergoes a redox reaction and the current in an electrochemical cell. A surface acoustic wave biosensor is a biosensor based on the measurement of resonant frequency of the surface acoustic wave. Various types of biosensors have been developed including the combinations of different types of biosensors, for example, an amperometric-potentiometric biosensor that includes both amperometric method and potentiometric method in detecting cell growth.

Several prior arts have disclosed applications related to construction of MEMS biosensors for detecting cell growth. One of the prior art is U.S. Pat. No. 5,135,852 which discloses a piezoelectric biosensor for detecting metabolic growth requirement, antibiotic responses and specific bacterial products of microorganisms. Generally, the more sensing methods integrated into a biosensor device enhances the performance of the biosensor device. However, this prior art utilizes only one type of sensing method in the biosensor which is a piezoelectric biosensor to observe the change in resonant frequency in order to detect the mass change of the living organism. Therefore due to the patent limited applicability, it is said to be not feasible in constructing a MEMS biosensor for detecting cell growth.

U.S. Pat. No. 5,981,268 has disclosed an apparatus and method for monitoring changes in cells upon addition of an analyte to the environment of the cell. In this prior art, only one detecting method is used, which is by monitoring the impedance changes of the cell, to detect the changes in the cell. This prior art has its drawbacks due to the limited sensing methods as more sensing methods can be integrated into one biosensor to monitor the change of a cell more accurately. Therefore due to the patent limited applicability, it is said to be not feasible in constructing a MEMS biosensor for detecting cell growth.

SUMMARY OF THE INVENTION

In accordance with the present invention, there is provided a MEMS biosensor device with an analysis platform for detecting cell growth using two different biosensing techniques. The MEMS biosensor device is a MEMS (microelectromechanical system) biosensor that combines microelectronic technology and biotechnology to obtain information on stiffness and adhesion of normal and cancer cell. Furthermore, this invention provides analysis platform for in vitro study and diagnosis of cancer cells. The two biosensing techniques used in the MEMS biosensor are shear horizontal-surface acoustic wave (SH-SAW) resonator and electric cell-substrate impedance sensing (ECIS) technique where the shear horizontal-surface acoustic wave (SH-SAW) resonator is used to monitor the resonant frequency of the resonator and the electric cell-substrate impedance sensing (ECIS) technique is used to record impedance spectra of different subcellular regions of a single cell. This biosensor is able to simultaneously perform these two different types of electric measurements on the same cell in real time. In this present invention, the preferred embodiment comprises of an aluminium nitride (AlN) base, a shear horizontal-surface acoustic wave (SH-SAW) resonator including an input transducer and an output transducer, a counter electrode, a plurality of working electrodes, an impedance analyzer and a back-etched silicon substrate. The aluminium nitride (AlN) base is used to hold the input transducer, the output transducer, the working electrodes and the counter electrode, and is coupled to the back-etched silicon substrate. As for the impedance analyzer, it is electrically connected to the working electrodes and the counter electrode in order to record the impedance spectra of the living cell. The shear horizontal-surface acoustic wave (SH-SAW) resonator having an input transducer and an output transducer that is symmetrically positioned on the aluminium nitride (AlN) base, are used respectively for transmitting surface acoustic wave towards the living cell and receiving surface acoustic wave from the living cell. The working electrodes of the electrode cell-substrate impedance sensing (ECIS) technique are placed on the acoustic path of the shear horizontal-surface acoustic wave (SH-SAW) resonator and are used to receive frequency voltage from the living cell. As for the counter electrode of the electric cell-substrate impedance sensing (ECIS) technique, it is placed parallel to these working electrodes and is used for transmitting frequency voltage towards the living cell. The growth of the living cell can be monitored through the shift of the resonant frequency from the shear horizontal-surface acoustic wave (SH-SAW) resonator where the growth of the living cell changes the parameters of the resonant frequency. As by using electric cell-substrate impedance sensing (ECIS) technique, the living cell obstructs the current flowing from the living cell to the working electrode and therefore causing an increase in the impedance measurement. By using this MEMS biosensor, the whole cell can be mapped in terms of cell stiffness, adhesion and cell viscoelasticity.

It is a benefit of this present invention to provide a MEMS biosensor device that uses shear horizontal-surface acoustic wave (SH-SAW) resonator and electric cell-substrate impedance sensing (ECIS) technique in detecting cell growth.

It is another benefit of this present invention to provide a MEMS biosensor device that is able to perform two different types of electric measurements simultaneously on the same living cell in real time.

It is yet another benefit of this present invention to provide a MEMS biosensor device that is able to provide information on the stiffness and adhesion of normal and cancer cell.

It is further another benefit of this present invention to provide a MEMS biosensor device that is able to constitute an analysis platform for in vitro study and diagnosis of cancer cell.

BRIEF DESCRIPTION OF DRAWINGS

A complete understanding of the present invention may be obtained by reference to the accompanying drawing, when considered in conjunction with the subsequent, detailed description in which.

DETAILED DESCRIPTION OF DRAWINGS

Figure 1A:
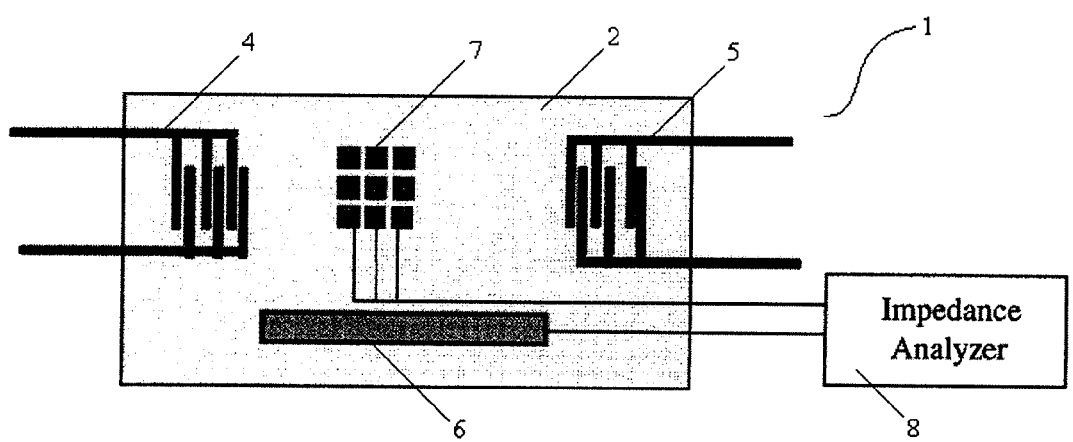
FIGS. 1A and 1B is the top view and side view of the MEMS biosensor.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims. For ease of reference, common reference numerals will be used throughout the figures when referring to the same or similar features common to the figures.

Figure 1B:
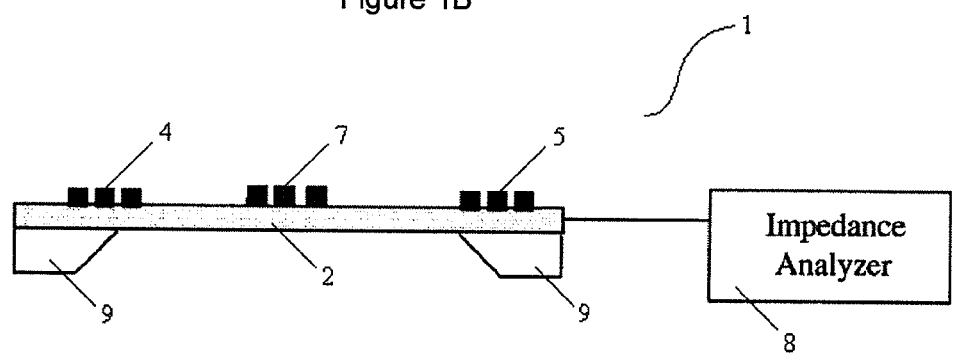

Referring to FIGS. 1A and 1B, a MEMS biosensor device (1) comprises of an aluminium nitride (AlN) base (2) coupled with a piezoelectric thin film, a shear horizontal-surface acoustic wave (SH-SAW) resonator having an input transducer (4) and an output transducer (5) that are symmetrically positioned on the aluminium nitride (AlN) base (2), a counter electrode (6) positioned parallel to working electrodes (7) on the aluminium nitride (AlN) base (2) for transmitting frequency voltage towards a living cell (3), a plurality of working electrodes (7) positioned beneath the living cell (3) on the aluminium nitride (AlN) base (4) for receiving frequency voltage from the living cell (3), an impedance analyzer (8) for receiving impedance readings from the counter electrode (6) and working electrodes (7), and a back-etched silicon substrate (9) coupled to the aluminium nitride (AlN) base (2) for reducing current loss. The aluminium nitride (AlN) base (2) having the piezoelectric thin film is used to hold the input transducer (4), the output transducer (5), the counter electrode (6), the working electrodes (7) and the living cell (3). The piezoelectric thin film provides an electric field to the aluminium nitride (AlN) base (2) so that the surface acoustic wave can be transmitted and received by the input transducer (4) and output transducer (5) respectively. The aluminium nitride (AlN) base (2) is coupled to a back-etched silicon substrate (9) in order to reduce current loss. The shear horizontal-surface acoustic wave (SH-SAW) resonator comprises of the input transducer (4) and the output transducer (5) where these input transducer (4) and output transducer (5) are positioned symmetrically on the aluminium nitride (AlN) base (2). The input transducer (4) transmits surface acoustic wave with the resonant frequency around 100 MHz towards the living cell (3) whereby the output transducer (5) receives the surface acoustic wave from the living cell (3) in terms of resonant frequency. Shear horizontal-surface acoustic wave (SH-SAW) resonator is used due to the minimal damping of the acoustic wave in liquid. The shear horizontal-surface acoustic wave (SH-SAW) resonator correlates the relationship between the electrical measurements and mechanical properties of the living cell (3). The living cell (3) attached above the working electrodes (7) on the aluminium nitride (AlN) base (2) with growing activities produces changes in the parameters of the equivalent circuit that consequently changes the resonant frequency. As for the electric cell-substrate impedance sensing (ECIS) technique, it comprises of the counter electrode (6) and the plurality of working electrodes (7). The working electrodes (7) are positioned in between the input transducer (4) and the output transducer (5), and the counter electrode (6) is positioned parallel to these working electrodes (7) where the counter electrode (6) is used to transmit frequency voltage towards the living cell (3) and the working electrodes (7) are used to receive frequency voltage from the living cell (3). The counter electrode (6) and the working electrodes (7) are electrically connected to the impedance analyzer (8) to receive impedance readings from the counter electrode (6) and working electrodes (7). When the living cells (3) are placed above the working electrodes (7) on the aluminium nitride (AlN) base (2), the electrical impedance of the working electrodes (7) increases due to the fact that more current has to bypass the living cell (3). With the living cell (3) acting like an insulating body, the living cell's (3) shape or fluctuations of the living cell (3) will increase the impedance of the working electrodes (7). Therefore, impedance measurements can be performed to monitor the growth of the living cell (3).

Figure 2:
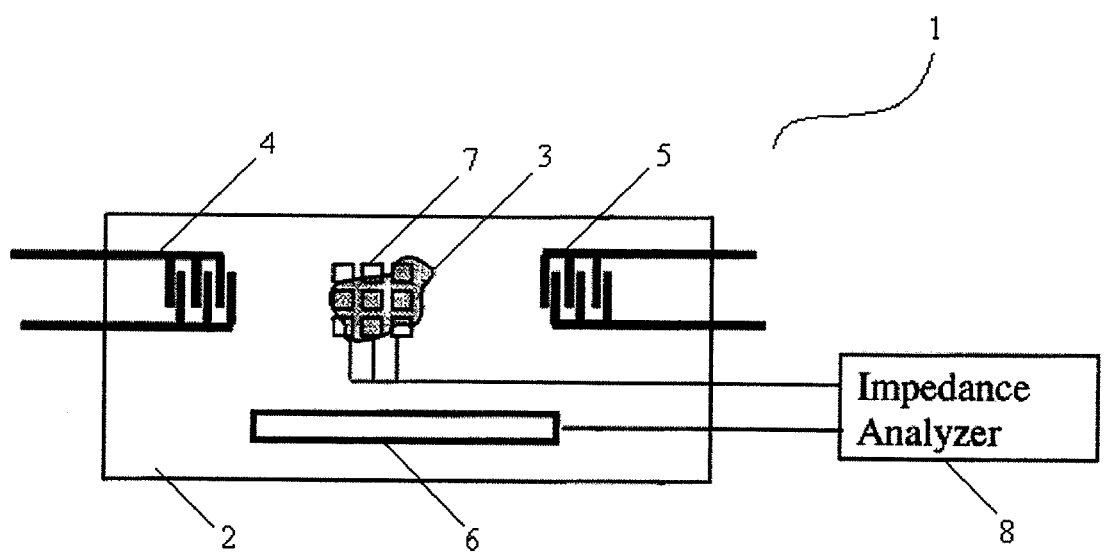
FIG. 2 is the top view of the MEMS biosensor with a living cell attachment.

Referring to FIG. 2, it is showing a MEMS biosensor (1) having the living cell (3) attached above the working electrodes (7) on the aluminium nitride (AlN) base (2) where the living cell (3) can be a single normal cell or cancer cell. The working electrodes (7) are gold electrodes that are patterned in an array of small electrodes with the dimensions of 2 µm×2 µm. Each of the working electrodes (7) is covered with extracellular matrix protein layer to promote cell adhesion. The working electrodes (7) are not in contact with each other. This is to collect information corresponding to subcellular regions of the living cell (3). Each working electrode (7) supports a different subcellular region of the living cell (3), giving information about the stiffness and attachment of that particular region of the living cell (3). The impedance measurements are performed using a small ac electric field over a wide frequency range of 100 Hz to 100 kHz. The impedance analyzer electrically connected to the counter electrode (6) and working electrodes is used to apply periodic voltage signals of variable frequency to the counter electrode (6) and working electrodes (7). The impedance is calculated as the ration of voltage phasor, U(jω), and the current phasor, I(jω) as shown in the equation below, $$Z(j\omega) = \frac{U(j\omega)}{I(j\omega)} = Z_{re}(\omega) + jZ_{im}(\omega)$$

where $j=\sqrt{-1}$, $\omega=2\pi f$ and f is the excitation frequency in Hz. The magnitude and the phase angle of the impedance measurement are, $$|Z| = \sqrt{Z_{re}^2 + Z_{im}^2}$$

$$\varphi = \arctan\left(\frac{Z_{im}}{Z_{re}}\right)$$

Figure 3:
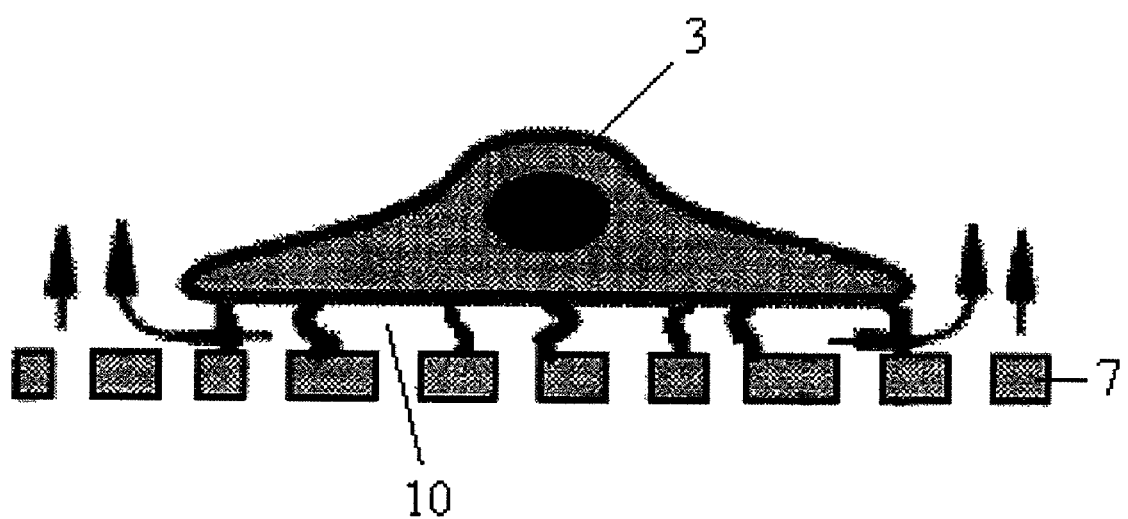
FIG. 3 is the side view of the attachment of the living cell on the working electrodes.

Referring to FIG. 3, it is showing the living cell (3) attachment on the working electrodes (7) with focal adhesion contacts and current flowing through the gap (10) between the living cell (3) and the working electrodes (7). The average gap (10) between the living cell (3) and the working electrodes (7) surface is 50 nm to 150 nm. At low frequencies, current flow from regions beneath the living cell (3) and through the gap (10) with no change in measured impedance. At moderate frequencies, the living cell (3) obstructs the current flow and therefore causing an increase in the impedance measurement.

We claim:

1. A biosensor device (1) providing an analysis platform for detecting cell growth, comprising of:
    an aluminium nitride (AlN) base (2) coupled with a piezoelectric thin film;
    a shear horizontal-surface acoustic wave (SH-SAW) resonator including an input transducer (4) and an output transducer (5) symmetrically positioned on the aluminum nitride (AlN) base (2);
    a counter electrode (6) positioned parallel to working electrodes (7) on the aluminum nitride (AlN) base (2), for transmitting frequency voltage towards the living cell (3) and is electrically connected to an impedance analyzer (8);
    a plurality of working electrodes (7) positioned beneath the living cell (3) on the aluminium nitride (AlN) base (2) for receiving frequency voltage from the living cell (3) and are electrically connected to an impedance analyzer (8);
    an impedance analyzer (8) for receiving impedance readings from the counter electrode (6) and working electrodes (7); and
    a back-etched silicon substrate (9) coupled to the aluminium nitride (AlN) base (2), for reducing current loss;
    wherein the living cell (3) is positioned in between the input transducer (4) and output transducer (5) on the aluminium nitride (AlN) base (2).

2. A biosensor device (1) providing an analysis platform for detecting cell growth in claim 1 wherein the input transducer (4) provides means for transmitting shear acoustic wave towards the living cell (3).

3. A biosensor device (1) providing an analysis platform for detecting cell growth in claim 1 wherein the output transducer (5) provides means for receiving shear acoustic wave from the living cell (3).

4. A biosensor device (1) providing an analysis platform for detecting cell growth in claim 1 wherein the working electrodes (7) are gold (Au) electrodes.

5. A biosensor device (1) providing an analysis platform for detecting cell growth in claim 1 wherein the working electrodes (7) are covered with cell-extracellular matrix protein (ECM) layer for facilitating the living cell (3) attachment to these electrodes array.

6. A biosensor device (1) providing an analysis platform for detecting cell growth in claim 1 wherein the surface acoustic wave excitation is preferably at resonant frequency around 100 MHz.

* * * * *